US008394131B2

(12) United States Patent
Wing et al.

(10) Patent No.: US 8,394,131 B2
(45) Date of Patent: Mar. 12, 2013

(54) OCCIPITOCERVICAL FIXATION SYSTEM

(75) Inventors: Charles A. Wing, Center Valley, PA (US); Robert M. Crews, Memphis, TN (US); John A. Usher, Jr., West Palm Beach, FL (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1105 days.

(21) Appl. No.: 12/088,580

(22) PCT Filed: Sep. 25, 2006

(86) PCT No.: PCT/US2006/037385
§ 371 (c)(1),
(2), (4) Date: Aug. 13, 2008

(87) PCT Pub. No.: WO2007/041085
PCT Pub. Date: Apr. 12, 2007

(65) Prior Publication Data
US 2009/0270924 A1    Oct. 29, 2009

Related U.S. Application Data

(60) Provisional application No. 60/722,310, filed on Sep. 30, 2005.

(51) Int. Cl.
*A61B 17/70* (2006.01)
*A61B 17/58* (2006.01)

(52) U.S. Cl. ........................................ 606/280; 606/264

(58) Field of Classification Search ............... 606/70, 606/71, 246–279, 280–299, 300–331
See application file for complete search history.

(56) References Cited

U.S. PATENT DOCUMENTS

| 5,545,164 | A  | * | 8/1996  | Howland ...................... 606/250 |
| 5,582,612 | A  | * | 12/1996 | Lin .............................. 606/250 |
| 6,146,382 | A  | * | 11/2000 | Hurlbert ...................... 606/286 |
| 6,524,315 | B1 |   | 2/2003  | Selvitelli |
| 6,547,790 | B2 | * | 4/2003  | Harkey et al. ................ 606/250 |
| 6,620,164 | B2 | * | 9/2003  | Ueyama et al. .............. 606/261 |
| 7,232,441 | B2 | * | 6/2007  | Altarac et al. ................ 606/250 |
| 7,303,563 | B2 | * | 12/2007 | Poyner et al. ................ 606/279 |

(Continued)

FOREIGN PATENT DOCUMENTS

| EP | 1 180 348 A2 | 2/2002 |
| JP | 2002102241   | 4/2002 |

(Continued)

OTHER PUBLICATIONS

PCT International Search Report for International Application No. PCT/US2006/037385; Search Report Completed Feb. 5, 2007 and Mailed Feb. 19, 2007.

(Continued)

*Primary Examiner* — Kevin T Truong
*Assistant Examiner* — Christopher Beccia
(74) *Attorney, Agent, or Firm* — RatnerPrestia

(57) ABSTRACT

An occipital plate system comprising: (a) a plate having one or more apertures for receiving bone fasteners adapted for securing the plate to the skull; (b) two rails extending outwardly from opposing sides of the plate; and (c) two rod receptacles, each comprising a body portion and a receiver portion, the body portion defining a passageway through which one of the rails slides, the receiver portion defining a cavity to receive a rod and threads above the cavity for receiving a set screw such that at least a portion of each of a rail, the rod and the set screw are contained within the rod receptacle.

25 Claims, 7 Drawing Sheets

U.S. PATENT DOCUMENTS

| | | |
|---|---|---|
| 7,575,588 B2 * | 8/2009 | Barker et al. .................. 606/280 |
| 7,618,443 B2 * | 11/2009 | Abdou .......................... 606/278 |
| 7,695,500 B2 * | 4/2010 | Markworth .................... 606/280 |
| 7,776,070 B2 * | 8/2010 | Null et al. ..................... 606/252 |
| 7,901,433 B2 * | 3/2011 | Forton et al. .................. 606/250 |
| 2002/0143327 A1 * | 10/2002 | Shluzas ........................... 606/61 |
| 2003/0004512 A1 * | 1/2003 | Farris et al. ...................... 606/61 |
| 2003/0045878 A1 | 3/2003 | Petit |
| 2003/0125741 A1 * | 7/2003 | Biedermann et al. ............ 606/61 |
| 2003/0153913 A1 * | 8/2003 | Altarac et al. ................... 606/61 |
| 2005/0283153 A1 * | 12/2005 | Poyner et al. .................... 606/61 |
| 2005/0288669 A1 * | 12/2005 | Abdou ............................. 606/61 |
| 2007/0049932 A1 * | 3/2007 | Richelsoph et al. ............. 606/61 |
| 2007/0118121 A1 * | 5/2007 | Purcell et al. ................... 606/61 |

FOREIGN PATENT DOCUMENTS

| | | |
|---|---|---|
| WO | WO/98/41160 A | 9/1998 |
| WO | WO 2004/069038 A2 | 8/2004 |

OTHER PUBLICATIONS

Japanese Office Action dated Mar. 24, 2011 together with English Translation.

* cited by examiner

OCCIPITOCERVICAL FIXATION SYSTEM

REFERENCE TO RELATED APPLICATIONS

This application is a national stage of PCT Application No. PCT/US06/037385, filed Sep. 25, 2006 which claims priority to U.S. Provisional Application No. 60/722,310, filed on Sep. 30, 2005, which is hereby incorporated by reference.

FIELD OF THE INVENTION

The present invention is related to a system for stabilizing the spine. More particularly, the present invention is related to an occipital plate system, which secures a cervical fixation system to a patient's occiput.

BACKGROUND OF INVENTION

Occipitocervical fixation systems provide stabilization of the base of the skull (or occiput) with respect to the neck. To function effectively, occipitocervical fixation systems should meet a number of design criteria. For example, such systems must be extremely strong and rigid, yet be minimally invasive and have a low profile. Such systems should also be relatively easy to assemble, implant, and maintain. Although spinal systems for the lumbar and the thoracic areas of the spine have been developed to meet these design criteria, the occipitocervical area presents additional challenges for implantation given its smaller size and increased concentration of nerves and arteries which need to be identified and avoided. Moreover, there is less muscle mass in the occiput to cover the implant.

Occipitocervical fixation systems typically include an occipital plate, which is secured to the occiput of the skull, rods on either side of the spine, which are fixed to vertebrae with screws or hooks, and rod receptacles, which attach the rods to the occipital plate. Of particular interest herein are the occipital plate and rod receptacles, referred to herein collectively as the occipital plate system. Recently, occipital plate systems have been developed in which the plate and rod components are discrete to permit greater flexibility during installation. Such occipital plate systems thus function to secure the rods to the occiput of the skull, while allowing for adjustment of the rods relative to the plate before the system is "fixed" usually by tightening the rod receptacles in some fashion.

For example, U.S. Pat. No. 6,477,790 discloses a plate and rod junction mechanism for securing the rod to the plate. The mechanism comprises a bolt with a slot to receive the rod, a rod support platform that fits over the bolt, and a nut, which tightens down on the bolt to urge the rod against the support platform and into the plate. The base of the bolt is round to rotate freely in a counter-bored aperture of the plate. The support platform is a thick, annular washer that lies over the base of the bolt and has a rounded groove to receive the rod. When installed, the plate is sandwiched between the base of the bolt and the support platform.

Although recently-developed systems, such as that disclosed in the '790 patent, provide flexibility/configurability, applicants recognize that they tend to have small "contact area" by virtue of the bolt residing in a slot. As used herein, the term "contact area" refers to the interfacial surfaces between the rod and plate, which are subject to compressive force when the occipital plate system is fixed in place. Generally, there must be adequate contact area between the rod and the plate—either directly or via inserts/washers—such that once the system is tightened, there is no relative movement between the rod and the plate. In the system of the '790 patent, the intersection of the plate and the rod is limited to just a portion of the edge of the aperture in which the bolt resides. To compensate for this limited contact area, the system of the '790 patent uses the support platform to essentially expand the contact area of the device to make it adequate to resist movement.

Although the support platform in the '790 patent increases the contact area between the rod and the occipital plate, its use faces a number of drawbacks. For example, it adds another component to the occipital plate system, which, in turn, increases the complexity of the system and complicates its installation. Additionally, because the support platform encircles bolt, it adds bulk to system, which can be problematic given the restricted space of the occiput.

Therefore, there is a need for an occipital plate system which tightly secures the rod to the plate, but which avoids bulk and complexity. The present invention fulfills this need among others.

SUMMARY OF THE INVENTION

The present invention provides an occipital plate system having adequate contact area between the spinal rods and the plate to rigidly secure the two, while avoiding the complexity and bulk of external nuts and support platforms. To this end, the occipital plate system of the present invention is configured such that the contact area between the rod and the occipital plate lies within the confines of the rod receptacle. That is, rather than having a fastener slide within an aperture of the occipital plate (in which the contact area is limited to just a portion of the aperture's edge around the fastener), the present invention provides an occipital plate system in which a rail of the occipital plate slides within the rod receptacles.

This configuration provides for a number of benefits. First, the entire width of the rail is used as contact area in contrast to the prior art in which only the edge of the aperture about the fastener is used. This eliminates the need for a support platform or similar component to increase contact area, thereby simplifying the occipital plate system of the present invention and minimizing its size.

Additionally, since the rail does not need to accommodate an aperture for the bolt, a more slender rail can be used. This has the advantage of reducing the form factor of the occipital plate system which is critical in the confined space of the occiput. Furthermore, by reducing the size of the rails, a larger occipital plate can be used which has a larger surface with additional apertures for bone screws. A larger occipital plate with additional bone screws equates to a more robust connection to the skull.

Finally, the contact area between the rod and the occipital plate is situated directly below the set screw. This results in a direct line of contact among the components within the confines of the rod receptacle, thereby optimizing the compressive force imparted by the set screw and eliminating the need for an external nut as used in the prior art. This has the benefit of, not only maintaining a small form factor, but also optimizing the force of the set screw to hold the rod rigidly with respect to the plate.

Accordingly, one aspect of the invention is an occipital plate system in which the contact area between the plate and the spinal rods is internal to the rod receptacle. In a preferred embodiment, the system comprises: (a) a plate having one or more apertures for receiving bone fasteners adapted for securing the plate to the skull; (b) at least one rail extending outwardly from the plate; and (c) at least one rod receptacle, each comprising a body portion and a receiver portion, the body portion defining a passageway through which the rail slides, the receiver portion defining a cavity to receive a rod and threads above the cavity for receiving a set screw such that at least a portion of the rail, the rod and the set screw are contained within the rod receptacle. Preferably, at least a portion of the rail, rod and set screw overlap along a vertical axis, and, more preferably, the vertical axis is the center axis of the set screw.

DETAILED DESCRIPTION OF THE PREFERRED EMBODIMENTS

Figure 1A:
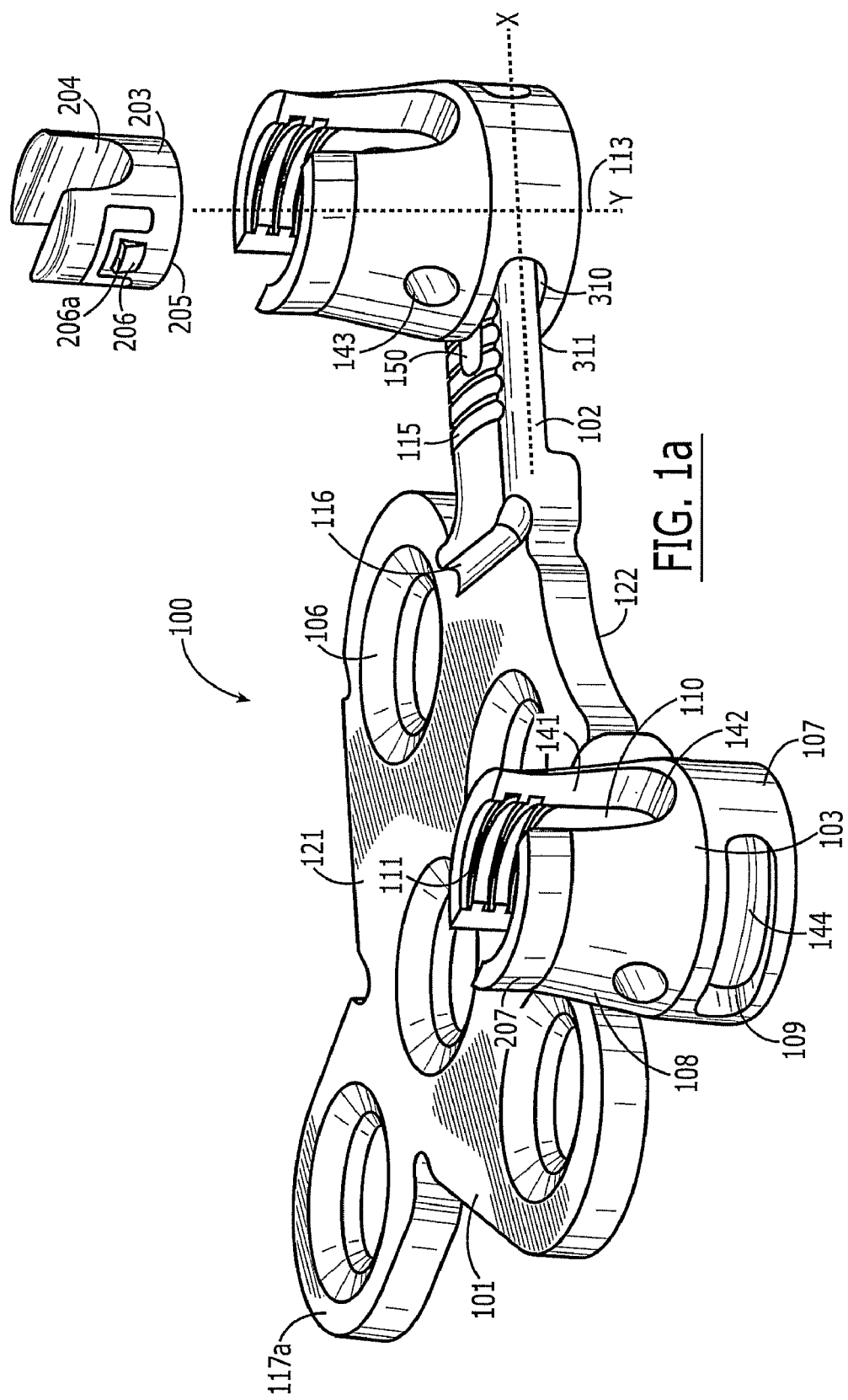
FIG. 1(a) shows a perspective view of a preferred embodiment of the occipital plate system of the present invention.
Figure 1B:
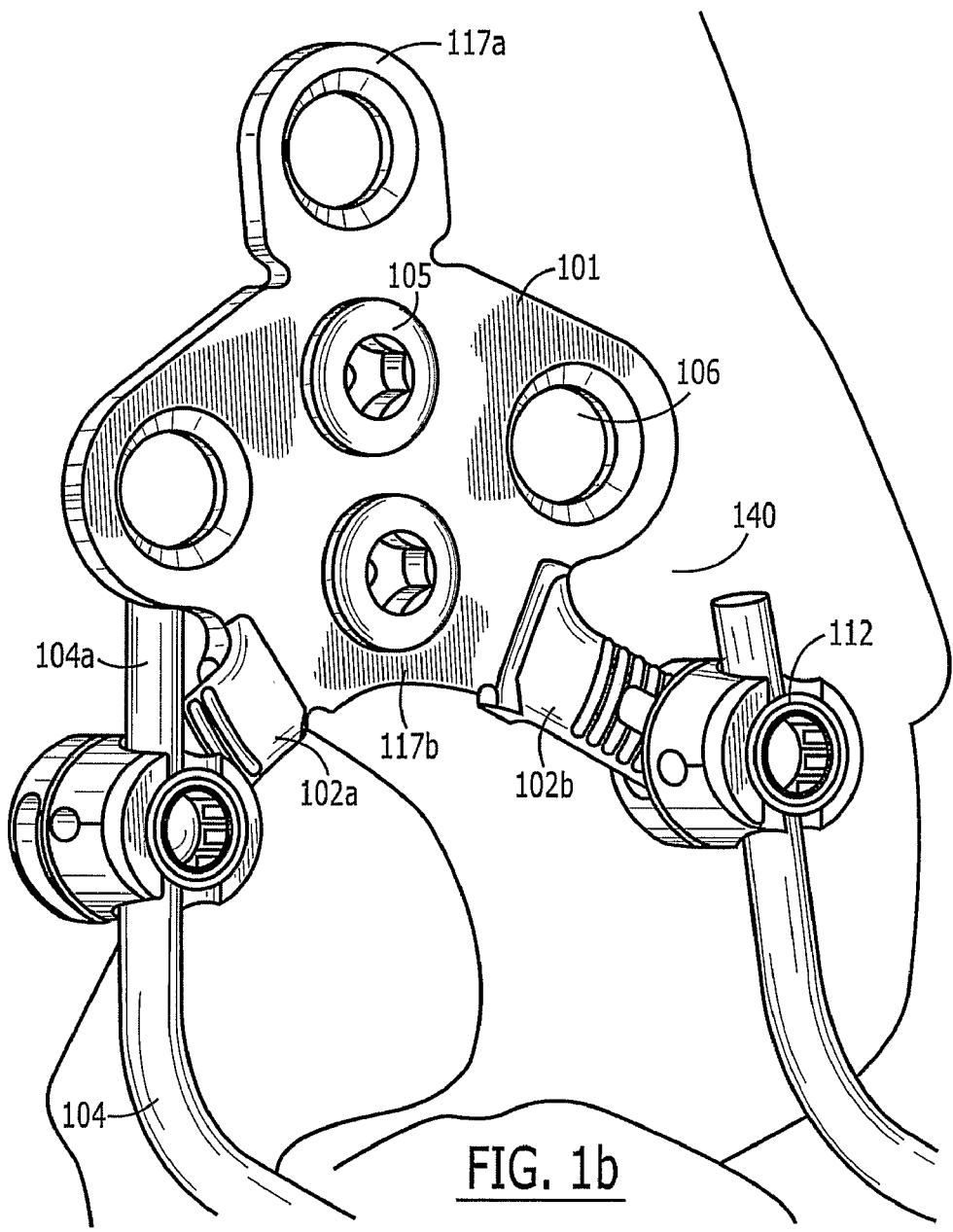
FIG. 1(b) shows a perspective view of the occipital plate shown in FIG. 1(a) implanted in a patient's occiput.

Referring to FIGS. 1(a) and 1(b) perspective views of a preferred embodiment of an occipital plate system 100 of the present invention are shown. The occipital plate system 100 is suitable for securing distal ends 104a of spinal rods 104 to the occiput of a patient's skull 140. For purposes of describing the relative position of various elements of the system, the system is deemed to have a top 121 (which, in FIG. 1 projects out of the page), a bottom 122 (which projects into the page), a superior end 117a (toward the top of the page), and an inferior end 117b (toward the bottom of the page). It should be understood that this orientation is for descriptive purposes only and should not be used to limit the scope of the invention.

The occipital plate system 100 comprises: (a) a plate 101 having one or more apertures 106 for receiving bone fasteners 105 adapted for securing the plate 101 to the patient's skull; (b) two rails 102a, 102b extending outwardly from the plate 101; and (c) two rod receptacles 103 each comprising a body portion 107 and a receiver portion 108. The body portion 107 defines a passageway 109 through which a rail 102a, 102b slides. The receiver portion defines a cavity 110 to receive the rod 104 and threads 111 above the cavity 110 for receiving a set screw 112. In this configuration, at least a portion of the rail 102a, rod 104 and set screw 112 are contained within the rod receptacle. Preferably, at least a portion of the rail 102a, rod 104 and set screw 112 overlap along a vertical axis, and, more preferably, the vertical axis is the center axis 113 of the set screw. Each of these elements is considered in detail below. It should be understood, however, that the categorization of the occipital plate system into these elements is done for descriptive purposes only and that it is within the scope of the invention to combine one or more of these elements into a common element or divide one or more of these elements into additional elements.

Occipital Plate

Figure 4:
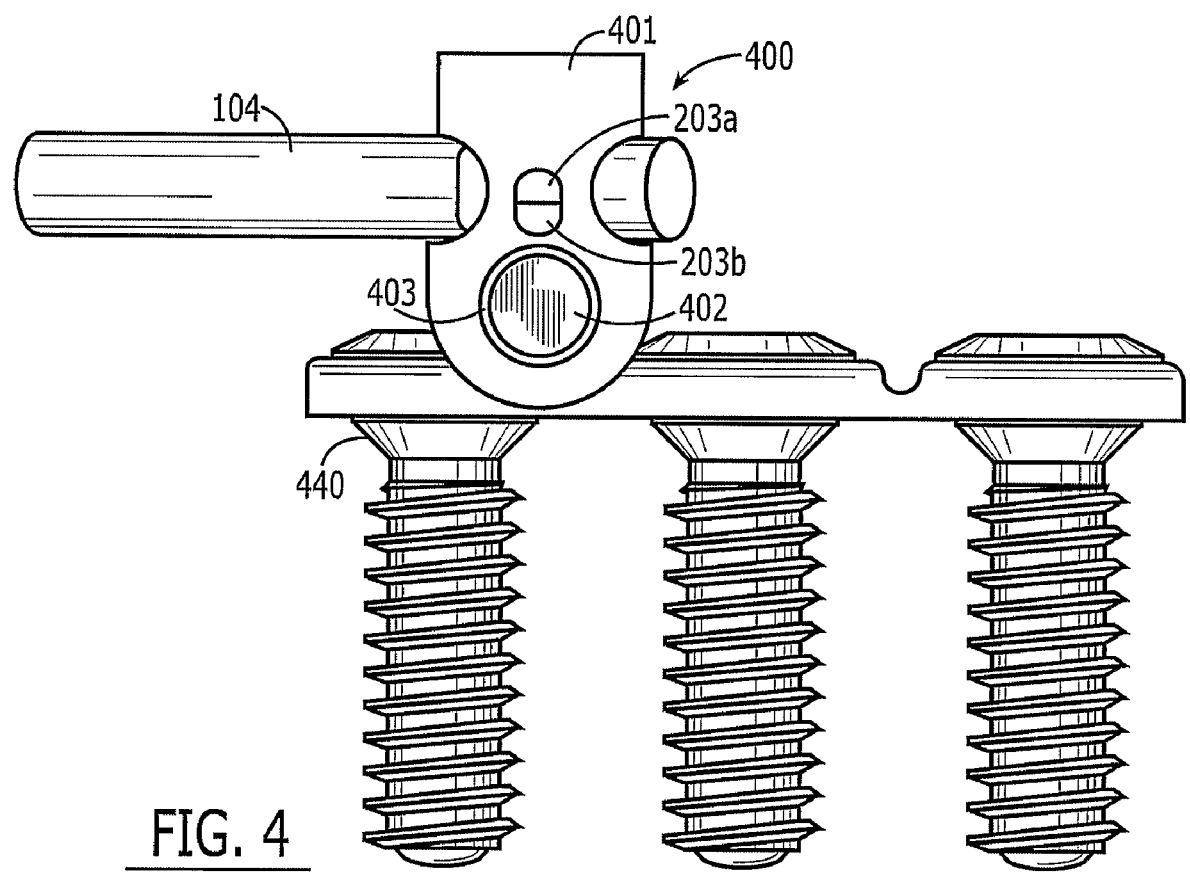
FIG. 4 shows a side view of an alternative embodiment of the occipital plate in which the rail has a circular cross section.

Referring to FIGS. 1a and 1b, the plate 101 will now be considered in detail. The plate 101 functions to secure the occipital system to the patient's skull. To this end, the plate comprises a number of apertures 106 configured to receive bone screws 105 as described above. Such bone screws are well known in the art and will not be discussed herein in detail. In a preferred embodiment, the screws comprise barbs 440 to engage the plate around the aperture once the screws have been screwed down as shown in FIG. 4. In a preferred embodiment, the screw heads are made to be flush with the top of the plate when installed.

It has been found that the bone mass along the centerline of the occiput tends to be relatively thick and provides the best purchase point for the bone screws. Accordingly, in a preferred embodiment, a number of apertures are located in the center of the occipital plate.

Preferably, the bottom side of the occipital plate is roughed to enhance its ability to stay put while being installed. A roughed surface also promotes the plate's integration with the bone of the skull.

Applicants have found that to accommodate the confined space of the occiput, the occipital plate should be bendable. To this end, in a preferred embodiment, the plate 101 comprises a number of crenulations 116 to allow portions of the plate to bend relative to other portions. In a preferred embodiment, these crenulations segregate the plate into various portions. For example, referring to the embodiment depicted in FIG. 2, the plate comprises a central portion 117 having superior and inferior ends 117a, 117b and a median portion 117c. From the median portion 117c extends side portions 119, 118 from which the rails 102a, 102b extend, respectively.

In addition to having the plate bendable, it may be preferable to have certain portions removable to accommodate the confined space of the occiput. To this end, in the embodiment of FIG. 2, the central portion comprises a tail portion 120 inferior to the median portion 117c. The tail portion is demarcated from the rest of the plate 101 by a tail crenellation 116a. This crenellation provides a convenient location to separate the tail portion 120 from the remaining plate 101 in the event there is insufficient room in the occiput.

Figure 5:
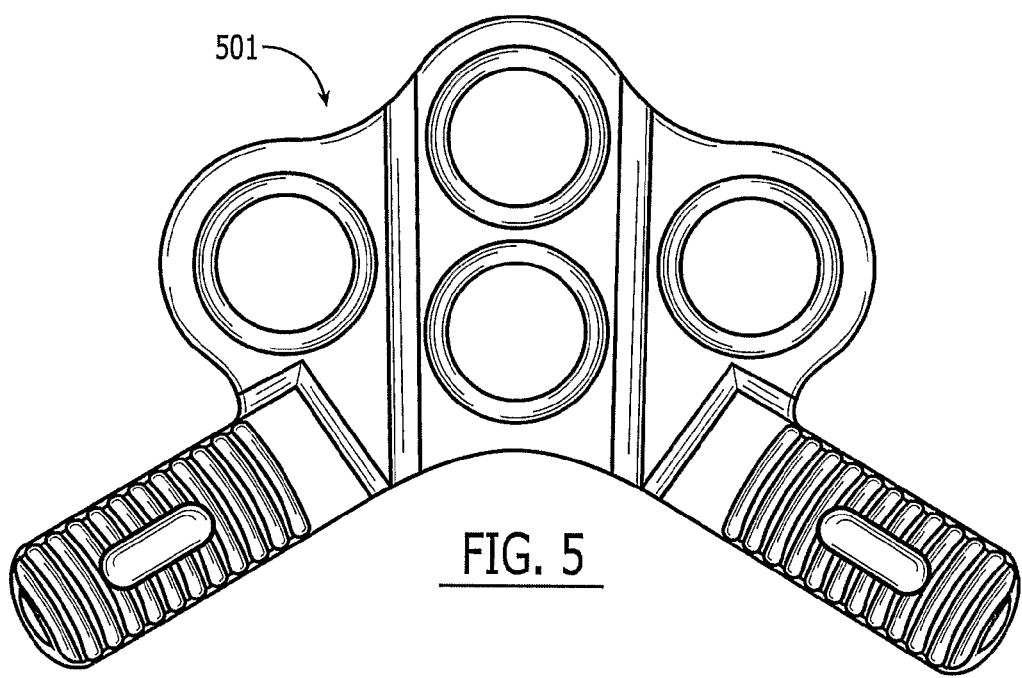
FIG. 5 shows an alternative embodiment of the occipital plate shown in FIG. 1(a).

Due to the slender nature of the rails extending from the plate (discussed below), there is sufficient room for the plate to accommodate additional bone screws in the side portions—either superior or inferior to the rails. Although it is generally preferable to increase the number of holes along the central portion of the plate as shown in FIGS. 1(a) and (b), it may be preferable in the case of smaller occiputs to reduce the size and number of screw holes in the plate. For example, referring to FIG. 5, an alternative embodiment of a plate 501 is show. This plate is smaller than those depicted in FIGS. 1(a) and 2, and has fewer bone screws. In light of this disclosure, one skilled in the art can configure alternative plate configurations and sizes within the scope of the invention.

Rails

Figure 2:
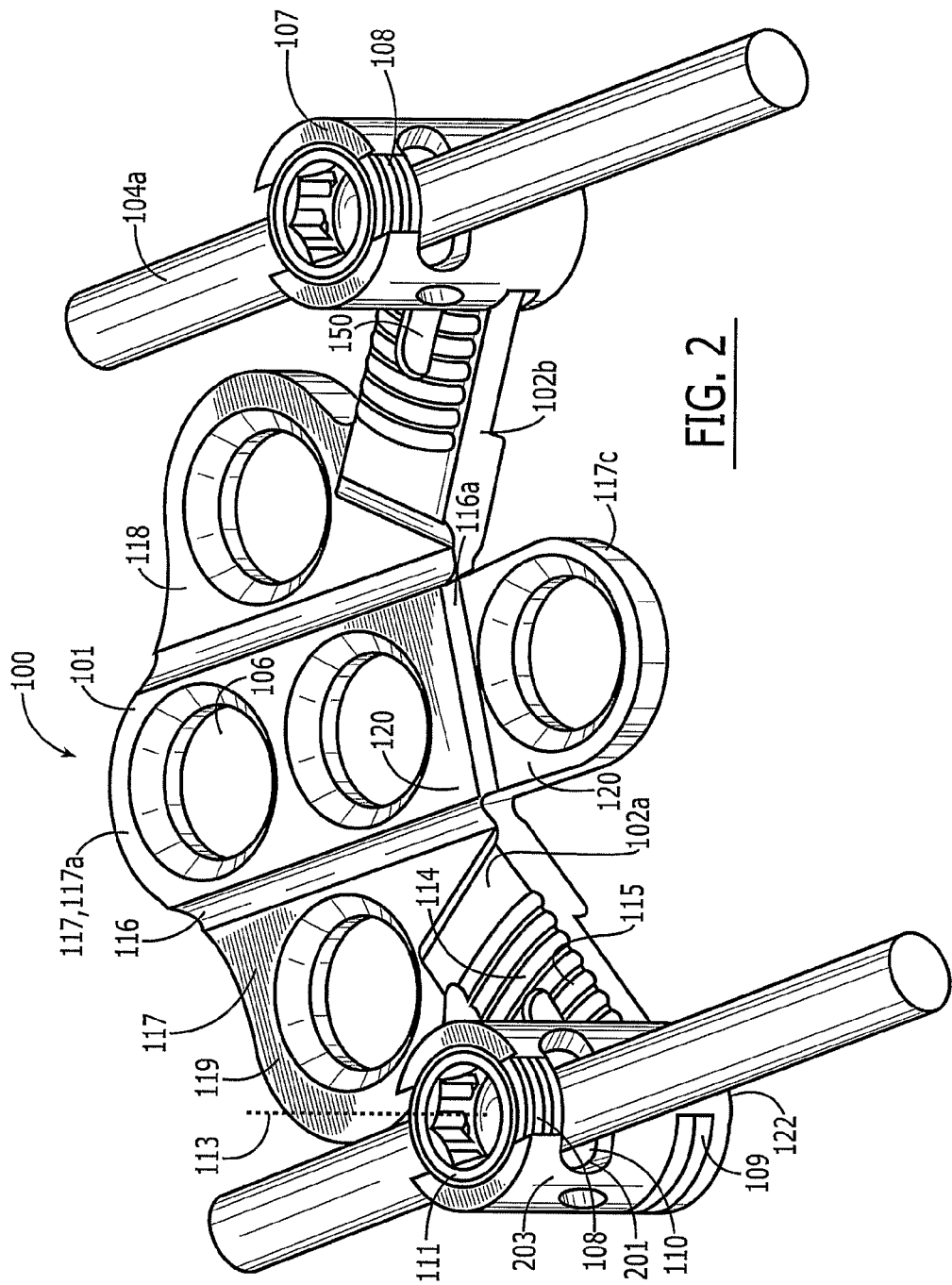
FIG. 2 shows a slightly different configuration of the occipital plate shown in FIG. 1(a).

Referring to FIGS. 1 and 2 the rails 102(a) & (b) are now considered in detail. The rails function to provide a variable connection point between the rod receptacle and the occipital plate. Preferably, the rails extend outwardly from the plate in approximately the same plane as the plate. Specifically, with respect to FIG. 1(b), the rails extend essentially outwardly and inferiorly from the inferior portion 117b of the plate. In the embodiment of FIG. 2, the rails extend from the bottom of the side portions 118, 119 of the occipital plate. Indeed, other configurations are possible within the scope of the invention. For example, the rails may extend interiorly from the side portions of the occipital plate before extending outwardly, the rails may extend outwardly before extending inferiorly, or they may curve or arc inferiorly and outwardly providing that the rod receptacle 103 is able to slide thereon.

As discussed in greater detail below with respect to the movement of the rod receptacle about the rails, in a preferred embodiment, the cross section of the rail is non-circular to prevent pivoting of the rod receptacle about the rail. Such non-circular cross sections include polygonal configurations and, preferably, a rectangular configuration. Most preferably, the rail cross section has a slender rectangular shape 144 as shown in cross section in FIG. 3. Such an embodiment is preferred for a number of reasons. First, it has a low profile in the top/bottom direction. This is critical since there is little room in the occiput to accommodate the height of the rod receptacle. In contrast, a round cross section, as shown in FIG. 4, raises the overall height of the rod receptacle, although a round cross section has other benefits as mentioned below.

Figure 3:
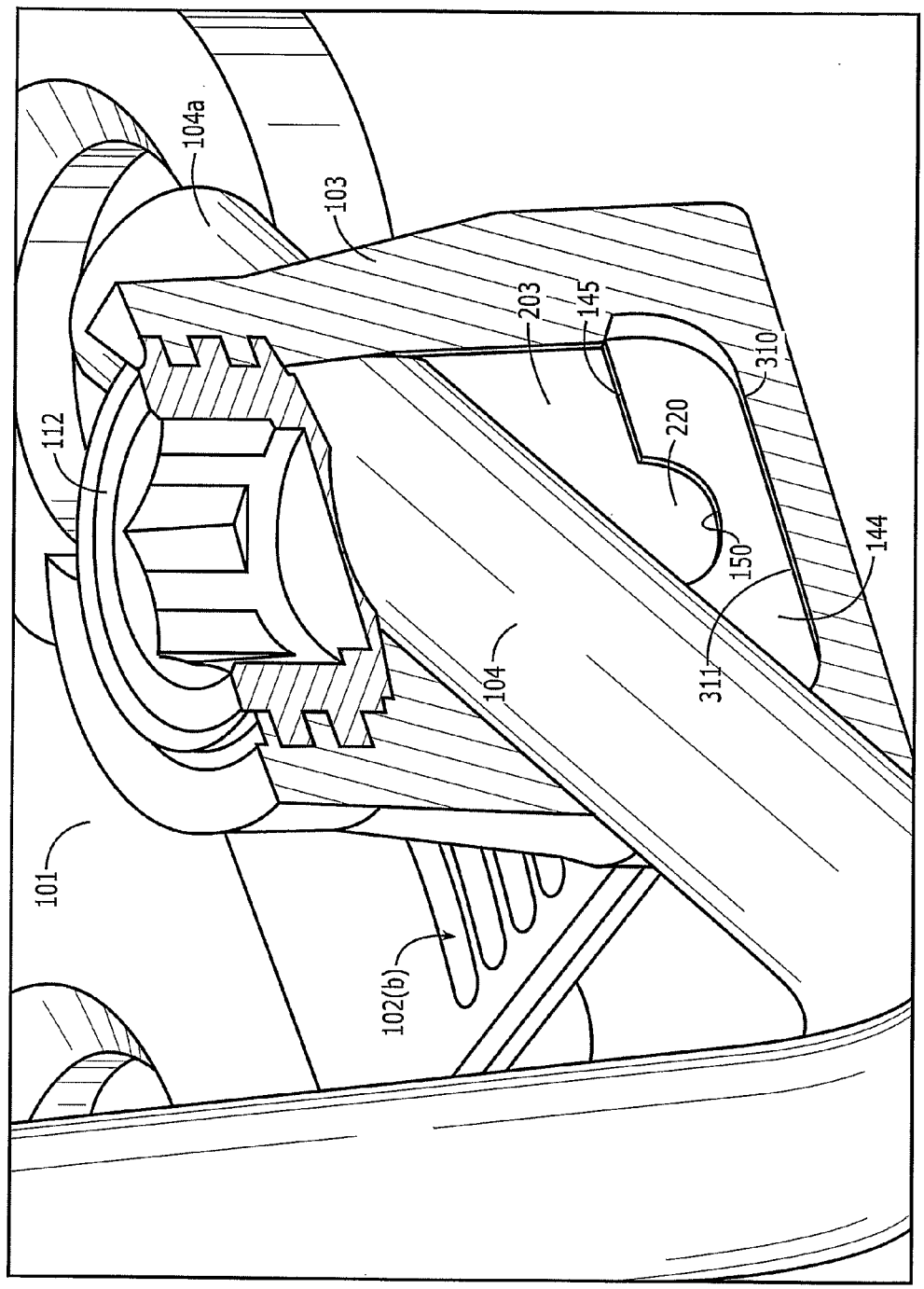
FIG. 3 shows a cross section perspective view of the rod receptacle of the occipital plate of FIG. 1(a).

Additionally, aside from its low profile, the slender rectangular rail provides a planar top surface 145 (see FIG. 3). A planar top surface is preferred not only because it prevents rotation about the rail, but also because it provides a large contact area. The large surface provides an excellent base upon which an insert 203 or even the rod 104 can seat as opposed to, for example, a round rail 402 in which the contact surface would be limited to just a thin line at the top of the rail absent the use of an insert. Finally, the planar surface acts as a bearing surface on which the insert 203 or rod 104 can readily pivot. In contrast, the convex surface provided by a round rail 402 would not facilitate pivoting of an insert thereon unless the insert were split to provide a planar bearing surface as described below.

Although not necessary, it may be preferable to configure the occipital plate system such that, once the rod receptacles are disposed on the rails they cannot slide off. Such a configuration facilitates implantation since the surgeons need not concern themselves with holding all the components together while attempting to secure the rods to the plate. To this end, in one embodiment, the distal end of rail 102 is deformed once the rod receptacle is slideably mounted thereon to prevent the rod receptacle from sliding off. This deformation may be achieved by swaging the distal end of each rail once the rod receptacles are slid on to create a protrusion to prevent the rod receptacles from sliding back off. Swaging and other techniques to deform or otherwise produce a protrusion or surface anomaly that interferes with the sliding motion of the rod receptacles are well known techniques.

Alternatively, rather than deforming the rail, the rail may comprise an interior grove 150 running a portion of its length. Referring to FIG. 3, this interior groove 150 is configured to receive a protrusion 220 extending downward from the insert 203 (described in detail below). Thus, when the rod receptacle 103 is on the rail 102(*b*) and the insert 203 is in the rod receptacle, the protrusion 220 from the insert is disposed within the groove 150. As mentioned below, in a preferred embodiment, an insert snaps into the rod receptacle to hold it within the rod receptacle. Preferably, the axial movement of the insert within the rod receptacle is limited once it is snapped in place such that the protrusion is prevented from leaving the interior groove. Thus, the protrusion of the insert remains trapped by the interior groove, thereby holding the rod receptacle on the rail while allowing it to slide.

In a preferred embodiment, the rails are integrally formed with the plate, although it is within the scope of the invention that the rails be discrete from the plate. For example, it may be preferable that the rails be independently moveable with respect to the occipital plate such that they can be adjusted to fit the space of a patient's occiput. Furthermore, it is contemplated that the rails may be a portion of larger members that extend from the sides of the plate. For example, each rail may comprise a raised ridge along a larger arm.

Rod Receptacles

The function of the rod receptacle is to facilitate movement of the rod relative to the plate in one state, but to affix the position of the rod relative to the plate in another state. The first state is defined as the condition before the set screw is tightened and the second state is defined as the condition after the set screw is tightened. To describe the motion of the rod to the plate, it is convenient to orient the rod receptacle with respect to two axes—an x axis which runs along the rail and a y axis which runs essentially along the central axis of the rod receptacle. These axes are indicated in dotted lines in FIG. 1(*a*). In a preferred embodiment, the rod receptacles 103 are identical, thus, any description of one rod receptacle herein applies as well to the other rod receptacle.

As mentioned above, each rod receptacle comprises a body portion 107 and a receiver portion 108. The receiver portion functions to receive and secure the rod 104. In a preferred embodiment it has a cylindrical or taper cylindrical wall 207, defining a cavity 110 and rod openings 142 to accommodate the rod. In a preferred embodiment, the cylindrical wall 207 also comprises slots 141 extending from the rod openings 142 to the top 121 of the receiver portion. The slots 141 are sized to receive the rod 104 to allow the rods to be slid into the receiver portion from the top instead of being threaded through the rod openings 142. The receiver portion also comprises threads 111 which cooperate with threads on set screw 112. Accordingly, the treads 111 are located internally to the cylinder wall 207 above the cavity 110. In a preferred embodiment, the screw mechanism of the receiver portion is essentially the same as that disclosed in U.S. application Ser. Nos. 10/124,945 and 10/369,158, which are hereby incorporated by reference.

The body portion 107 of the rod receptacle functions to attach the receiver portion to a rail of the occipital plate. Specifically, the passageway 109 of the body portion 107 slideably receives the rail. Alternatively, rather than having the passageway envelope the rail, it may be preferable for the passageway to be open on one or more side. For example, the passageway may be c-shaped, providing that enough of the body portion 107 envelops the rail to secure the rod receptacle to the rail. In a preferred embodiment, the body and receiver portions are integrally formed as shown in FIGS. 1(*a*) and 2. Alternatively, the two portions may be discrete as shown in FIGS. 6(*a*) and (*b*).

Referring back to FIG. 1(*a*), to increase the contact area between the rod and the plate, the preferred embodiment of the occipital plate system 100 comprises an insert 203. The insert serves as an interface between the round rod and the rail of the occipital plate. To accommodate the round rod, the insert 203 comprises a concave surface 204. Opposite the concave surface 204 is a surface 205 complementary to the top surface 115 of the rail 102(*a*). In a preferred embodiment, as discussed below, the top surface of the rail is planar and, thus, the bottom of the insert would be planar as well.

For embodiments in which the rail 402 has a rounded top surface as shown in FIG. 4, it is preferable that the insert between the rod and the rail be split. That is, since the rod is adapted to pivot about the y axis when the rod receptacle is in its first state, the insert must be suitable for accommodating this movement. To this end, a split insert having a first half 203a for interfacing with the rod and a second half 203b for interfacing with the rail is preferred. The first and second halves are similar in form in that both comprise a concave surface for receiving the rail or the rod, and their opposite surface would be planar for interfacing with the planar surface of the other insert half. Thus, as the rod pivots about the y axis, the first and second insert 203a, 203b will pivot relative to one another on their planar surfaces.

Referring back to FIG. 1(a), insert 203 is preferably configured to snap into the rod receptacle to hold it in place. In this embodiment, the insert 203 has a resilient counter-levered arm 206 with a protrusion 206a on the free end thereof. The rod receptacle 103 has an aperture 143 for receiving the protrusion 206a. When the insert is pushed downwardly in the rod receptacle 103, the counter-leveled arm 206 deflects inwardly until the protrusion 206a aligns with the aperture 143. At this point, the resiliency of the arm 206 snaps the protrusion 206a into the aperture 143 to hold the insert in the rod receptacle. Preferably, the axial movement of the insert 203 (i.e., its up and down movement), is limited such that its protrusion 220 as shown in FIG. 3 stays in groove 150. It should be understood that other snapping mechanisms can be used. For example, rather than having the resilient arm disposed on the insert, the arm may be disposed on the rod receptacle and the protrusion may be disposed on the insert.

It may also be preferred to use a second insert to interface between the rod and the set screw 112. For example, the second insert may comprise a concave surface for interfacing with the rod 104 and an opposite surface for interfacing with the set screw. Presuming that the end of the set screw is planar, the opposite surface of the second insert would also have a planar surface.

To increase the rigidity of the rod relative to the occipital plate in its second state (i.e., after the set screw is tightened), it is preferable to enhance the surface of the rail 102 and possibly the surface of the rod 104 to increase friction or facilitate mechanical interlocking. For example, it is preferable to contour the top surface of the rails 102a, 102b with grooves 115. Additionally, in a preferred embodiment, the insert comprises a material which deforms upon compression by the set screw to protrude into the contours of the contoured surface. Suitable materials include, for example, pure titanium or PEEK. Preferably, the material is essentially pure titanium. Alternatively, rather than designing the insert to be softer than the rail, the rail may be designed to be softer than the insert. A suitable material for a hard insert may be, for example, cobalt chromium.

The rod receptacle of the present invention can be configured to provide for a great deal of flexibility in its relevant movement with respect to the plate. That is, it can be configured to move about any axis or to be stationary about any axis. The degree of freedom of the rod receptacle is a question of preference.

Generally, it is preferable that the rods move (slide) relative to the plate along the x axis (i.e., along the rail). Such movement allows the physician to adjust the lateral position of the rods relative to the spine, which is important as it avoids the need to bend the rods. Bending the rods is generally undesirable as it interrupts the surgical procedure and weakens the system, possibly leading to failure. Lateral movement is afforded by the sliding relationship of the rails 102a, 102b within the passageway 109.

Although freedom of movement between the rod and the occipital plate is generally desired, the desire for the rod receptacle to pivot about the x axis in the first state is outweighed by the need to have absolute rigidity about this axis in the second state. Consequently, rather than configuring the rail to have a circular cross section to facilitate rotation of the rod receptacle around the x axis (see, for example, the rail of the occipital plate depicted in FIG. 4), it is preferable to provide a rail with a non-circular cross section 144 to prevent such rotation.

Although preventing the body portion from pivoting about the x axis is preferred, it is by no means outside the scope of the invention. For example, referring to FIG. 4, an occipital plate system 400 is shown in which the rod receptacle 401 is configured with a circular passageway 403 to accommodate a circular rail 402. Such a configuration allows rod receptacle 401 to pivot about rail 402 (i.e., about the x axis) when the rod receptacle is in its first state. In embodiments having circular rails, the body portion may alternatively resemble a conventional pipe clamp having a resilient strap which is disposed about the round rail. This strap is tightened to prevent movement about the x axis in the second state. Such pipe clamps are known and are used, for example, in scaffolding and as pipe hangers.

It is also preferable for the rod to pivot about the y axis. Again, such movement allows the physician to adjust the relative position of the rods to the plate without the need to bend the rods. The degree to which the rod can pivot with respect to the plate in the first state is referred to herein as the pivot angle. It has been found that a minimum pivoting angle of about 5° is preferred, about 15° is more preferred, and about 20° is still more preferred The present invention contemplates various mechanisms by which the desired minimum pivot angle can be achieved. These pivoting mechanisms can be categorized as those that effect (1) pivoting of the rod receptacle relative to the rail, (2) pivoting of the rod relative to the rod receptacle, and (3) pivoting of the receiver portion relative to the body portion.

Referring to FIGS. 1(a) and 1(b), an example of the first category of pivoting mechanisms is illustrated. As shown, the passageway 109 defined in the body portion flares out at either end to allow the body portion 106 to pivot on the rail 102. The degree to which the passageway 109 flares out defines the extent of the pivot angle in the first state.

Securing this mechanism in the second state is illustrated in FIG. 3. The force applied by the set screw 112 causes the rod 104 to urge against the insert 203, which in turn urges against the rail 102(b), thereby imparting an upward, reactive force on the entire rod receptacle 103. This upward reactive force urges the bottom 310 of the body portion 108 against the bottom 311 of the rail 102(b). This contact plus the contact of the insert against the rail prevents movement of the body portion with respect to the rail in the second state.

This configuration is beneficial for several reasons. First, the rod is held rigidly in the receiver portion since the rod opening is closely fitted about the rod. In other words, there is no opportunity for the rod to move or pivot with respect to the receiver portion in the first or second state. Furthermore, since the contact area between the bottom 310 of the body portion and the bottom 311 of the rail is large compared to prior art contact areas, it tends to provide greater rigidity in the second state relative to other systems.

Referring to FIG. 2, an example of the second category of pivoting mechanisms is illustrated. The pivoting motion about the y axis is afforded by elongated opening 201 in the receiver portion 108. The elongated openings are longer than the diameter of the rod 104 to allow the rod to pivot in the receiver portion in the first state. Therefore, rather than having the entire rod receptacle pivot on the rail, the radial position of the rod receptacle on the rail is fixed, while the rod pivots within the receiver portion.

Referring to FIG. 4, an embodiment of the second pivoting mechanism is shown with a rail having a circular cross section. The way in which this mechanism secures the rod relative to the plate in the second state is essentially the same as in the embodiment shown in FIG. 3. Briefly, the set screw (not shown) is tightened down causing the first and second inserts 203a, 203b containing the rod 104 to urge against the rail 402 and thereby secure the rod to the rail.

The second category of pivoting mechanisms is advantages in that the rod receptacle is always rigid with respect to the plate in either the first or second state.

Figure 6A:
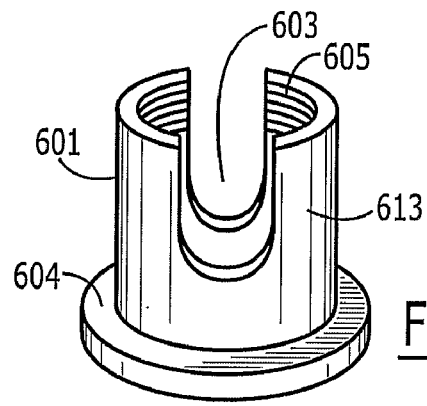
FIGS. 6(a)-(c) show alternative embodiment of the rod receptacle.
Figure 6B:
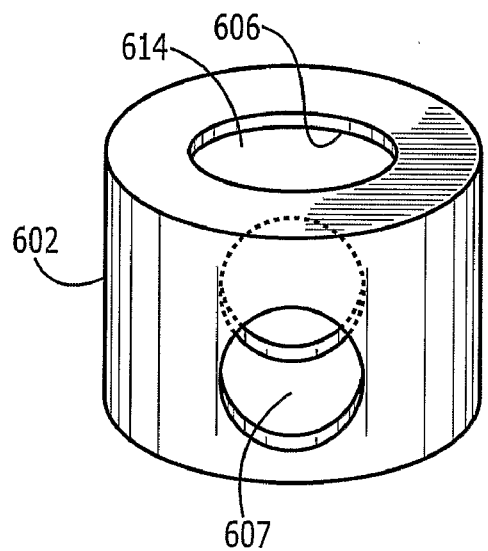
Figure 6C:
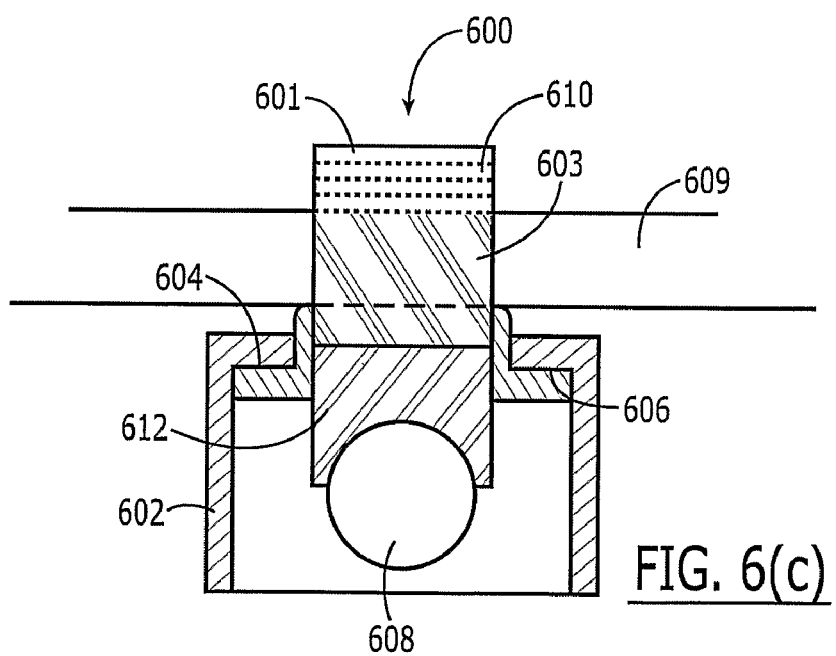

The third category of pivoting mechanisms is shown in FIGS. 6(a)-(c). Here, the pivoting between the rod and plate is achieved by the receiver portion 601 pivoting with respect to the body portion 602 in the first state. The retainer portion 601 is configured to receive the rod 609 snugly in the rod slot 603—as in the embodiment of FIG. 1(a)—while the body portion 602 receives the rail 608 snugly in passageway 607—as in the embodiment of FIG. 2. The retainer portion, however, is configured to move within the body portion in the first state. More specifically, the retainer portion 601 in this embodiment is inserted in the body portion 602 such that the cylindrical wall 613, which defines the rod slot 603, passes through a top opening 614 of the body portion 602. When assembled, the first bearing surface 604 of the retainer portion rides on the second bearing surface 606 of the body portion, thereby allowing the receiver portion 601 to rotate within the body portion in the first state.

To interface the rod with the rail, inserts 611 and 612 are preferred, which are the same as the first and second inserts 203a, 203b described above with respect to FIG. 3. Briefly, insert 611 is concave at the top to accommodate a rod and flat on the bottom to interface with insert 612. Likewise, insert 612 is concave on the bottom to accommodate the round rail 608 and flat on the top to interface with the insert 611. The two flat surfaces of the inserts are free to slide on each other in the first state when the retainer portion (and the rod) is rotated relative to the body portion (and the rail). It should be clear that if the top of the rail is planar then the second insert 612 is not necessary, and just one insert can be used in the embodiment shown in FIG. 1.

This configuration offers a number of advantages including, for example, a high-integrity, mechanically-interlocked union between the rod and the receiver portion and between the rail and the body portion. Additionally, this configuration provides a rigid union between the receiver and body portions when the rod receptacle is in its second state. This rigidity is based on two mechanisms. First, as in the embodiment depicted in FIG. 1, when the set screw is tightened, it urges against the rod, which, in turn urges against the inserts 611, 612 which, in turn, urges against the rail to essentially lock these components in relative position as discussed above. However, unlike the previously-considered embodiments, the receiver and body portions also engage along their respective bearing surfaces. Specifically, since the receiver portion is discrete from the body portion, the downward force applied by the set screw in effect causes the receiver portion to rise relative to the body portion such that the first bearing surface 604 of the receiver portion and the second bearing surface 606 of the body portion contact each other to prevent the relative movement of the components in the second state. In a preferred embodiment, these bearing surfaces are textured to enhance the frictional/mechanical interlocking.

It should be appreciated that the components of the occipital plate system described above are for illustrative purposes and that many variations can be practiced within the scope of the invention. Furthermore, it is anticipated that the various components described above can be mixed and matched for a particular application.

What is claimed is:

1. An occipital system for securing distal ends of spinal rods to a patient's skull, said occipital system having a top/bottom and superior/inferior orientation and comprising:
a plate having one or more apertures for receiving bone fasteners adapted for securing said plate to said skull;
at least one rail extending outwardly from said plate; and
at least one rod receptacle comprising a body portion, a vertical axis, and a receiver portion, said body portion defining a passageway which is encompassed by the body portion and slidably receives said rail therein, said receiver portion defining a cavity to receive a rod, and threads located above said cavity relative to the vertical axis and which receive a set screw,
wherein at least a portion of said rail, said rod, and said set screw are contained within said rod receptacle, and
wherein the passageway is disposed beneath the threads and the cavity relative to the vertical axis.

2. The system of claim 1, wherein said at least a portion of said rail, said rod and said set screw overlap along the vertical axis.

3. The system of claim 2, wherein said vertical axis is the center axis of said set screw.

4. The system of claim 1, wherein said body and receiver portions are integrally formed.

5. The system of claim 1, wherein said passageway includes a flared opening which facilitates rotation of said body portion on said one of said rails before said set screw is tightened down on said rod.

6. The system of claim 5, wherein said threads are internal.

7. The system of claim 5, wherein said receiver portion comprises a cylindrical wall defining slots extending normally from said elongated openings to the top of said receiver portion, said slots being sized to receive said rod.

8. The system of claim 1, further comprising an insert between said rod and said rail, said insert increasing contact area between said rod and said rail.

9. The system of claim 8, wherein said insert comprises a concave portion which receives said rod therein and a flat portion which contacts said rail.

10. The system of claim 9, wherein said insert comprises a resilient arm having a protrusion and said receiver portion comprises an aperture adapted to receive said protrusion,
wherein, when said insert is pushed into said receiver portion, said protrusion snaps into said aperture and secures said insert in said receiver portion.

11. The system of claim 10, wherein said rail comprises an interior groove extending in a lengthwise direction of the rail, and said insert comprises a bottom protrusion extending from its a bottom, said groove receiving said bottom protrusion therein.

12. The system of claim 8, wherein said rail comprises a contoured surface.

13. The system of claim 12, wherein said insert comprises a material which deforms upon a compression force applied by said set screw.

14. The system of claim 13, wherein said insert comprises pure titanium.

15. The system of claim 8, further comprising an upper insert located between said set screw and said rod, said upper insert comprising a concave portion which receives said rod therein and a flat portion which engages said set screw.

16. The system of claim 1, wherein said rails are integrally formed with said plate.

17. The system of claim 1, wherein said rail has a top planar surface.

18. The system of claim 1, wherein said plate comprises one or more crenulations defining bendable portions of said plate.

19. The system of claim 1, further comprising said rods.

20. The system of claim 1, further comprising said bone fasteners.

21. The system of claim 1, wherein there are two rails and two rod receptacles.

22. An occipital system for securing a distal end of one or more spinal rods to a patient's skull, said system comprising:
   a plate having a rail extending outwardly from said plate; and
   at least one rod receptacle slidable along the rail, the rod receptacle comprising a body portion, a vertical axis, and a receiver portion, said body portion defining a passageway encompassed by the body portion, and which slidably receives the rail therein through at least one side of the body portion, the body portion encompassing the rail, said receiver portion defining a cavity which receives a rod, and threads located above said cavity relative to the vertical axis and which receives a set screw therein,
   wherein at least a portion of said rail, said rod, and said set screw are contained within said rod receptacle, and
   wherein the rod received in the cavity is located above the rail slidably received in the passageway relative to the vertical axis, a longitudinal axis of the rod being oblique relative to a longitudinal axis of the rail.

23. The system of claim 1, wherein an outermost width of the rail along an entire length of the rail is less than a diameter of the passageway.

24. The system of claim 1, wherein an outermost diameter of the rail along an entire length of the rail is less than a diameter of the passageway.

25. An occipital system for securing distal ends of spinal rods to a patient's skull, said occipital system having a top/bottom and superior/inferior orientation and comprising:
   a plate having one or more apertures for receiving bone fasteners adapted for securing said plate to said skull;
   at least one rail extending outwardly from said plate;
   at least one rod receptacle comprising a body portion, a vertical axis, and a receiver portion, said body portion defining a passageway which is encompassed by the body portion and slidably receives said rail therein, said receiver portion defining a cavity to receive a rod, and threads located above said cavity relative to the vertical axis and which receive a set screw; and
   an insert provided within the at least one rod receptacle, wherein the rail comprises a groove defined thereon, and the insert comprises a protrusion extending therefrom, the groove configured to receive the protrusion therein,
   wherein at least a portion of said rail, said rod, and said set screw are contained within said rod receptacle, and
   wherein the passageway is disposed beneath the threads and the cavity relative to the vertical axis.

* * * * *

UNITED STATES PATENT AND TRADEMARK OFFICE
CERTIFICATE OF CORRECTION

PATENT NO. : 8,394,131 B2  Page 1 of 1
APPLICATION NO. : 12/088580
DATED : March 12, 2013
INVENTOR(S) : Wing et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1364 days.

Signed and Sealed this
First Day of September, 2015

Michelle K. Lee
*Director of the United States Patent and Trademark Office*